United States Patent
Chanbasha et al.

(10) Patent No.: US 9,146,218 B1
(45) Date of Patent: Sep. 29, 2015

(54) FULLY AUTOMATED ANALYTICAL METHOD FOR DETERMINATION OF CHLOROETHERS IN WATER AND URINE SAMPLE

(71) Applicants: KING FAHD UNIVERSITY OF PETROLEUM AND MINERALS, Dhahran (SA); KING ABDULAZIZ CITY FOR SCIENCE AND TECHNOLOGY, Riyadh (SA)

(72) Inventors: Basheer Chanbasha, Dhahran (SA); Mousa Yaser Amayreh, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 0 days.

(21) Appl. No.: 14/254,350

(22) Filed: Apr. 16, 2014

(51) Int. Cl.
*C07C 43/00* (2006.01)
*G01N 30/72* (2006.01)
*C07C 41/34* (2006.01)
*G01N 30/02* (2006.01)

(52) U.S. Cl.
CPC .......... *G01N 30/7206* (2013.01); *C07C 41/34* (2013.01); *G01N 2030/025* (2013.01)

(58) Field of Classification Search
CPC .................................................. C07C 43/137
USPC ....................................................... 568/676
See application file for complete search history.

(56) References Cited

U.S. PATENT DOCUMENTS 5,273,655 A    12/1993   Del Mar
2008/0199972 A1    8/2008   Sellrie

OTHER PUBLICATIONS

Huang et al. Determination of haloethers in water by solid-phase microextraction. Journal of Chromatography A, vol. 769, 1997, 239-246.*
Vatinno et al. Automated high-throughput method using solid-phase microextraction-liquid chromatography-tandem mass spectometry for the determination of ochratoxin A in human urine. Journal of Chromatography A, vol. 1201, 2008, 215-221.*
Kotowska, et al. Environmental Monitoring and Assessment 184 (5): 2893-2907 May 2012.
Guimaraes, et al. International Journal of Environmental Analytical Chemistry 88 (3): 151-164 2008.
Wennrich, et al. ACTA Hydrochimica ET Hydrobiological 25 (6): 329-334 Nov. 1997.

* cited by examiner

*Primary Examiner* — Sikarl Witherspoon
(74) *Attorney, Agent, or Firm* — Oblon, McClelland, Maier & Neustadt, L.L.P.

(57) ABSTRACT

A fully automated flow assisted-solid-phase microextraction (FA-SPME) is developed for the determination of chloroethers in aqueous samples. A CTC CombiPAL autosampler coupled with gas chromatography-mass spectrometry (GC-MS) is used to automate the extraction process. In this method, the SPME fiber is exposed to a sample in direct immersion. After exposure, the fiber is desorbed at the injection port of GC-MS.

9 Claims, 8 Drawing Sheets

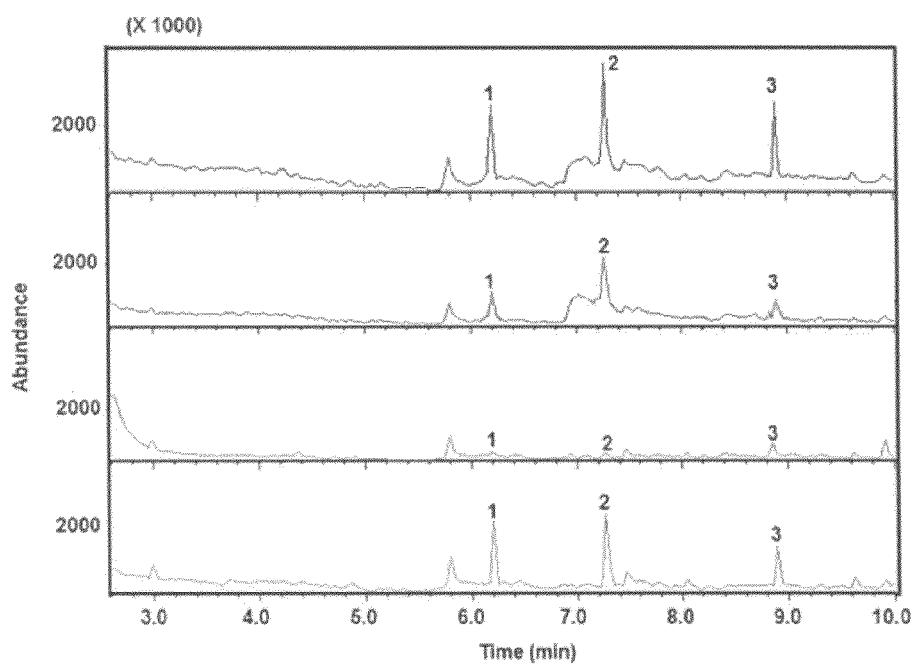

FULLY AUTOMATED ANALYTICAL METHOD FOR DETERMINATION OF CHLOROETHERS IN WATER AND URINE SAMPLE

BACKGROUND OF THE INVENTION

1. Technical Field

The present invention relates to a flow assisted-solid phase microextraction/gas chromatography-mass spectrometry (FA-SPME/GC-MS) system and a method for using the FA-SPME/GC-MS in which contacting, desorbing and determining analyst content are carried out consecutively.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Chloroethers (CEs) are compounds which contain an ether moiety (R—O—R) and halogen atoms attached to the aryl or alkyl groups. CEs are produced in significant quantities (more than 50 million pounds per year) and are commonly used as solvents in various industrial applications (C. Chiing-Chen, W. Ren-Jang, Y. I.-Chun, L. Chung-Shin, J. Hazard. Mater 172 (2009)1021; C. Jing-Shan, H. Shang-Da, Talanta 71 (2007) 882; M. Sittig, Handbook of Toxic and Hazardous Chemicals and Carcinogens, third ed., Noyes Public, New Jersey, 1991—each incorporated herein by reference in its entirety). Significant quantities of CEs are produced and utilized in the industry. Generally, CEs are stable and non-biodegradable in aqueous samples.

Bis(2-chloroethyl)ether (BCEE), bis(2-chloroisopropyl) ether (BCIE) and Bis(2-chloroethoxy)methane (BCEM) are a class of CEs frequently found in drinking water and urine (H. Sahng-Da, T. Chun Yi, L. Cheng-Shium, J. Chromatogr. A 769 (1997) 239; R. C. Dressman, J. Fair, E. F. Mcfarren, Environ. Sci. Technol. 11(1977) 719; I. H. Suffet, P. R. Cairo, J. Environ. Sci. Heal. A13 (1978) 117; R. D. Lingg, W. H. Kaylor, S. M. Pyle, M. M. Domino, Envirom. Con. Tox. 11 (1982) 173—each incorporated herein by reference in its entirety). Thus, the release of CEs into the environment is of great concern because of their toxicity and carcinogenicity (J. K. Fawell, S. Hunt, Environmental Toxicology: Organic Pollutants, Wiley, New York, 1988 (Chapter 9); L. Wennrich, W. Engewald, P. Poppb, lnrern J. Environ. Anal. Chem. 73(1998) 31—each incorporated herein by reference in its entirety). The United Sates Environmental Protection Agency (USEPA) and the International Agency for Research on Cancer have classified CEs as a carcinogenic compound category D (Wisconsin Department of Natural Resources Drinking Water & Groundwater Quality Standards/Advisory Levels, March 2011, incorporated herein by reference in its entirety).

The volatility and water solubility of BCEM may result in human exposure by inhalation, ingestion or dermal contact in the course of occupational exposures. The minimum half-life of BCEM in water has been reported to be 2 years (S. R. Black, K. S. Decosta, P. R. Patel, J. M. Mathews, Xenobiotica 37 (2007) 427; W. R. Haag, T. Mill, SRI Project No. 6877-1, Menlo Park, Calif., USA., (1989) 20—each incorporated herein by reference in its entirety) presenting the potential for persistent environmental exposure.

In this regard, different preconcentration methods have been reported for the analysis of CEs in water samples which includes USEPA methods 611 and 625 based on liquid—liquid extraction (LLE). However, LLE procedures require large volumes of hazardous organic solvents and multi-step extractions which are time-consuming and involve the risk of analyte loss in the extraction and concentration processes and not suitable for trace level determination (A. Mousa, C. Basheer, A. R. Al-Arfaj, Talanta 115 (2013) 308—incorporated herein by reference in its entirety). The solid-phase extraction (SPE) is a solvent minimized alternative to the LLE approach, SPE-$C_8$, which was used for CEs. The main problem associated with SPE-$C_8$ is the low selectivity of the retention mechanism of CEs which yielded low recoveries (E. Chladek, R. S. J. Marano, Chromatogr. Sci. 22 (1984) 313.—incorporated herein by reference in its entirety).

In recent years, microextraction techniques for CEs have produced an important development in trace level analyses from various environmental samples. Liquid-phase microextraction (LPME) and solid-phase microextraction (SPME) are alternative microextraction methods for CEs (Y. He, H. K. Lee, Anal. Chem. 69 (1997) 4634; Y. Wang, Y. C. Kwok, Y. He, H. K. Lee, Anal. Chem. 70 (1998) 4610—each incorporated herein by reference in its entirety). LPME is a solvent minimized extraction technique in which CEs are extracted using immiscible organic solvents. The selection of suitable organic solvents for polar analytes and fully automation of LPME are challenging tasks.

Solid-phase microextraction (SPME) is a widely used solvent-free extraction microextraction technique which combines sampling, sample clean-up and pre-concentration into a single step (G. Ouyang, D. Vuckovic, J. Pawliszyn, Chem. Rev., 111(2011), 2784—incorporated herein by reference in its entirety). On the other hand, SPME requires careful calibration for the quantization of trace level analytes. This requires more time (J. Pawliszyn, Ed. Applications of Solid Phase Microextraction; RSC Chromatography Monographs: Cambridge, U.K., 1999—incorporated herein by reference in its entirety). Manual SPME optimization methods allow for human error and the possibility of contamination associated with manual processing (R. Vatinno, D. Vuckovic, C. G. Zambonin, J. Pawliszyn, J. Chromatogr. A 1201, (2008) 215—incorporated herein by reference in its entirety). Automated sample preparation eliminates human intervention in order to improve overall sample analysis efficiency and reliable robustness of the method (D. Vuckovic, Trends Anal. Chem., 45 (2013), 136—incorporated herein by reference in its entirety).

The present disclosure describes an automated flow assisted solid-phase microextraction (FA-SPME) combined with GC-MS in order to quantify CEs in large volume samples. SPME automation has been widely used in various modes such as headspace-SPME, direct immersion-SPME, and different formats which includes thin film-SPME, in-tip-SPME and 96 vial plate-SPME (B. Bojko, E. Cudjoe, G. A. Gomez-Rios, K. Gorynski, R. Jiang, N. Reyes-Garcas, S. Risticevic, E. A. S. Silva, O. Togunde, D. Vuckovic, J. Pawliszyn, Anal. Chim. Acta. 750 (2012) 132; W. Xie, J. Pawliszyn, W. M. Mullett, B. K. Matuszewski, J. Pharm. Biomed. Anal. 45 (2007) 599; D. Vuckovic, X. Zhang, E. Cudjoe, J. Pawliszyn, J. Chromatogr. A, 1217 (2010) 4041). In general, SPME automation has been reported only for small volume samples.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

In one embodiment of the disclosure, a flow assisted-solid phase microextraction/gas chromatography-mass spectrometry (FA-SPME/GC-MS) method is described.

In another embodiment the method includes directly contacting an SPME fiber with an aqueous sample to form an enriched SPME sample wherein the aqueous sample further comprises one or more chloroethers and the contacting is carried out in a flowing stream of the aqueous sample.

In another embodiment the method includes desorbing an analyte composition from the enriched SPME sample.

In another embodiment the method includes determining the content of one or more chloroethers in the analyte composition with GC-MS.

In another embodiment the desorbing is carried out inside a sample port of a gas chromato graph.

In another embodiment the desorbed analyte composition is chromatographed in the gas chromatograph.

In another embodiment the aqueous sample is passed over the SPME fibers only one time and is not recirculated over the SPME fiber.

In another embodiment the contacting, desorbing and determining are carried out consecutively.

In another embodiment the FA-SPME is fully automated and no manual operation is required during the extraction process.

In another embodiment the sample size has a total volume of 100 mL or more.

In another embodiment the SPME fiber is a Carbowax/Divinylbenzene fiber.

In another embodiment a flow assisted-solid phase microextraction/gas chromatography-mass spectrometry (FA-SPME/GC-MS) system is described.

In another embodiment the system includes a sample container that includes a sample solution containing an aqueous solution and analytes.

In another embodiment the system includes a first tube that connects the sample container and a pump and transports the sample solution to the pump.

In another embodiment the system includes a pump that that contacts and an SPME fiber with an aqueous sample comprising one or more chloroethers to form an enriched SPME sample.

In another embodiment the system includes a second tube that transports sample solution to an extraction vial.

In another embodiment the system includes an autosampler that uses the extraction vial to extract a sample through an automated SPME method to determine the analyte content in the sample.

In another embodiment the system includes a gas-chromatograph that desorbs the SPME fiber and determines the content of one or more chloroethers in the analyte composition.

In another embodiment the system includes a third tube that circulates sample from the extraction vial to the sample container.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIGS. 8A-8D demonstrate the total ion chromatograms of three CEs in real samples extracted by a fully automated FA-SPME/GC-MS system.

DETAILED DESCRIPTION OF THE EMBODIMENTS

Figure 1:
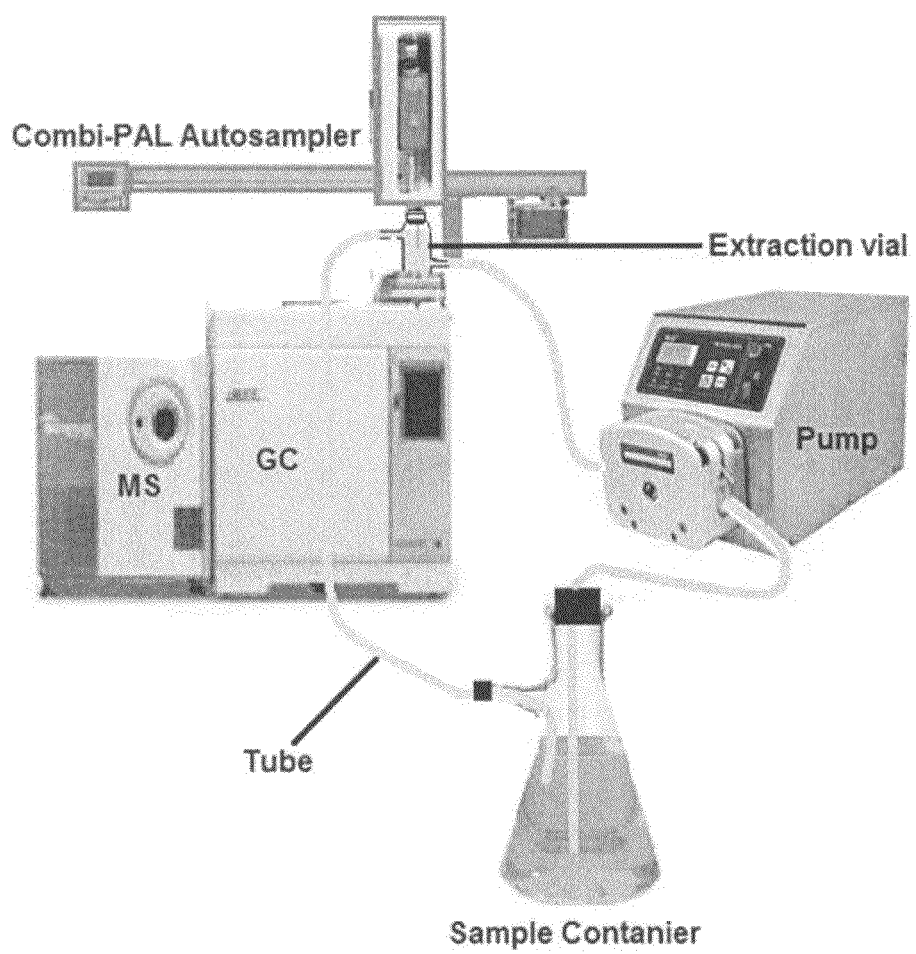
FIG. 1 is a schematic of an automated FA-SPME/GC-MS system.

Referring now to the drawings, wherein like reference numerals designate identical or corresponding parts throughout the several views.

In one embodiment, the present disclosure relates to a method for testing chloroether content in solution samples. First, in the method, a sample containing one or more chloroethers including but not limited to bis(2-chloroethyl)ether (BCEE), bis(2-chloroisopropyl)ether BCIE, and bis(2-chloroethoxy)methane (BCEM) is contacted with an SPME fiber adsorbent to adsorb the chloroether onto an SPME fiber. SPME fibers include but are not limited to polydimethylsiloxane (PDMS), carbowax/divinylbenzene (CW/DVB), and polyacrylate (PA).

After polymerization and cross-linking, solid PDMS samples present an external hydrophobic surface. This surface appears metallic and shiny, although the substrate is clear. This surface chemistry makes it difficult for polar solvents (such as water) to wet the PDMS surface, and may lead to adsorption of hydrophobic contaminants. Plasma oxidation can be used to alter the surface chemistry, adding silanol (SiOH) groups to the surface.

Solid PDMS samples will not allow aqueous solvents to infiltrate and swell the material. Thus PDMS structures can be used in combination with water and alcohol solvents without material deformation. Diisopropylamine swells PDMS to the greatest extent; solvents such as chloroform, ether, and THF swell the material to a large extent. Solvents such as acetone, 1-propanol, and pyridine swell the material to a small extent. Alcohols and polar solvents such as methanol, glycerol and water do not swell the material appreciably. The PDMS coated fiber used in the present disclosure has a matrix active group size in the range of 5-50 µm, 10-40 µm, or 20-35 p.m. Preferably the PDMS coated fiber has a matrix active group size of 30 µm.

The carbowax/divinylbenzene (CW/DVB) coated fiber has a coating compatibility to absorb analyte groups including but not limited alcohols and polar compounds. The carbowax/divinylbenzene coated fiber has a matrix active group size in the range of 40-80 µm, 50-75 µm, or 60-70 µm. Preferably the carbowax/divinylbenzene coated fiber has a matrix active group size of 65 µm.

The polyacrylate (PA) coated fiber is used in methods relating to chromatography and biofuels manufacturing and testing. The polyacrylate coated fiber has a coating compatibility to absorb analyte groups including but not limited to polar semivolatiles and other polar compounds. The polyacrylate coated fiber has a matrix active group size in the range of 60-100 µm, 70-90 µm, or 75-85 µm.

Preferably, the polar fiber CW/DVB is used.

Another embodiment of the invention includes extracting the analytes using the SPME fiber. Extraction of the analytes are performed by the SPME fiber in direct immersion mode at modified auto sampler vial for a time period in the range of 5-30 minutes, 7-25 minutes, or 8-15 minutes. Preferable, the analytes are extracted by the SPME fiber in direct immersion mode in the modified auto sampler vial for 10 minutes in a continuous flow mode. Preferably the samples are circulated at a flow rate in the range of 1-100 mL/min, 10-90 mL/min, or 30-80 mL/min per 1-50 $m^2$, 5-20 $m^2$, or 10-15 $m^2$ of surface area of the SPME fiber to allow for cholorether adsorption onto the SPME fiber. Preferably, the samples are circulated at a flow rate of 50 mL/min per 5 $m^2$ of surface area of the SPME fiber.

The pH of the sample solution is in the range of 2-12, 3-11, or 7-10. Preferably the pH of the sample is basic and has a pH of 10. The salt concentration of the sample solution is in the range of 0.1-20% (w/v), 8-18% (w/v), or 9-14% (w/v). The effect of ionic strength on the extraction efficiency is altered by adding NaCl concentrations ranging from 0-40% (w/v), 5-35% (w/v), or 10-30% (w/v). Preferably, NaCl is added to the solution at a concentration of 10% (w/v) as it allows for the highest extraction efficiency of the CEs. The sample solution including the chloroether is connected to a 20 mL modified auto sampler vial with flexible PEEK tubing.

Following extraction, the fiber is thermally desorbed in the gas chromatography-mass spectrometry (GC-MS) injection port in a time period in the range of 0-5 minutes, 1-4.5 minutes, or 2-4 minutes at a temperature in the range of 200-400° C., 225-375° C., or 250-300° C. Preferably the fiber is thermally desorbed in the GC-MS injection port for 3 minutes at 290° C.

In one embodiment of the invention the FA-SPME/GC-MS system is fully automated and no manual intervention is required during the extraction process.

EXAMPLES

A mixture of CEs standards were purchased from Supelco (Bellefonte, Pa., USA). This mixture, containing bis(2-chloroethyl)ether, bis(2-chloroisopropyl)ether and bis(2-chloroethoxy)methane at 2000 µg $mL^{-1}$. A working standard solution was prepared by appropriate dilution of stock solution of CEs in the same solvent (hexane). Physical and chemical properties of target analytes are shown in (Table 1). Table 1 is shown below.

Analytical grade solvents were purchased from Supelco (Bellefonte, Pa., USA). Double deionized water obtained from a Milli-Q system (Millipore, Bedford, Mass., USA). Sodium hydroxide, hydrochloric acid and sodium chloride were obtained (Merck, Darmstadt, Germany). To avoid any carryover of CEs; all laboratory glassware was washed with concentrated hydrochloric acid and rinsed with deionized water followed by acetone and dried out in the laboratory oven at 100° C. for 1 h. Precise peristaltic pump was purchased from J.P. Selecta (Abrera-Barcelona, Spain) provides flow rates from 20 to 200 mL $min^{-1}$. The speed can be automatically control through external controller.

Analyses were performed using a gas chromatograph (Agilent technologies, 7890A GC) coupled with a quadrupole mass selective spectrometer (Agilent technologies, 5975C) equipped with an inert ion source and provided with a split-splitless injection port. An A HP-5 GC fused silica capillary column (Agilent 19091J-413; 30 m×320 µm ID×0.25 thickness) was selected to separate the analytes. CTC CombiPAL autosampler (GC sampler 80, Zwingen, Switzerland) was used for the full automated FA-SPME. Ultra high purity helium (99.999%, Abdulah Hashim, Al-Khobar, Saudi Arabia) was used as the carrier gas at a flow rate of 1.3 mL $min^{-1}$. The samples were injected in the splitless mode. The temperature program used for the analyses was as follows: the initial temperature was 40° C. held 1 min which was then increased to 118° C. at 10° C. $min^{-1}$ and held for 3 min, then to 190 C at 15° C. $min^{-1}$ and held for 4 min. The total run time was 18.6 min. The injection port, ion source and interface temperatures were 280° C., 230° C., and 250° C., respectively. For qualitative determinations, the MSD was operated in full-scan mode from m/z 50 to 550 and selective ion monitoring mode was used for the quantification of the analytes.

Drinking and tap water samples were collected from main campus of King Fahd University of Petroleum and Minerals, Saudi Arabia. Urine sample were collected in cleaned glass bottles from a volunteer working at water desalination facility. All samples were stored at 4° C. prior to analysis.

Experimental setup of FA-SPME is shown in FIG. 1. FIG. 1 is a schematic of automated FA-SPME/GC-MS. A 100 mL sample solution spiked with CEs, sample pH 10 and salt concentration of 10% (w/v) was placed in a 125 mL flask and connected to 20 mL modified auto sampler vial with flexible PEEK tubing. Samples were circulated with different flow rates using peristaltic pump. Extractions were performed by SPME fiber in direct immersion mode at modified auto sampler vial for 10 min in a continuous flow mode. After the

TABLE 1

Physical properties of three CEs

| Physical properties | BCEM | BCEE | BCIE |
|---|---|---|---|
| Molecular structure | Cl~~O~~O~~Cl | Cl~~O~~Cl | (structure with Cl, O, Cl) |
| Molecular weight (g $mol^{-1}$) | 173 | 143 | 171 |
| Solubility at 20-25° C. (mg $L^{-1}$) | 1353.4 | 10200 | 1700 |
| Vapor pressure at 20-25° C. (mmHg) | 0.179 | 1.34 | 0.85 |
| Boiling Point (° C.) | 220 | 178 | 187 |
| Henry's law constant at 20° C. | 0.001 | 0.00089 | 0.004 |
| Diffusion coefficient in air ($cm^2$ $s^{-1}$) | 0.058 | 0.069 | 0.06 |
| Diffusion coefficient in water ($cm^2$ $s^{-1}$) | 7.11E−06 | 7.53E−06 | 6.40E−06 | extraction, the fiber was thermally desorbed in the GC-MS injection port for 3 min at 290° C.

Figure 2:
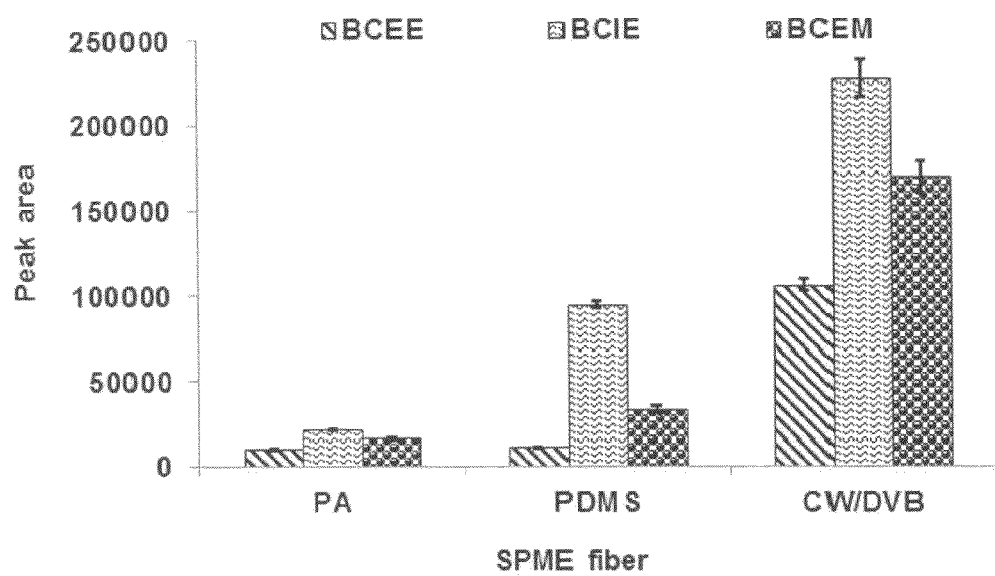
FIG. 2 is a graph of the selection of SPME fibers under specific extraction conditions.

To optimize the SPME conditions, three commercially available fibers were tested to extract CEs. Polydimethylsiloxane (PDMS, 30-μm), Carbowax/Divinylbenzene (CW/DVB, 65-μm) and polyacrylate (PA, 85-μm) coated fibers were purchased from Supelco (Supelco, Bellefonte, Pa., USA) and used without any modifications. The fibers were conditioned prior use according to the instructions provided by the suppliers. FIG. 2 is a graph of the selection of SPME fiber (extraction conditions; 100 mL of sample spiked with 100 μg $L^{-1}$ of CEs, absorption time 10 min, desorption time 3 min, sample flow rate of 40 mL $min^{-1}$ and sample pH of 5.7). FIG. 2 shows the extraction performance and CW/DVB give high peak areas for all CEs. And there is a high agreement with the fact that says more polar compounds are best extracted by polar fibres like CW/DVB. From the result CW/DVB fiber was finally selected for use in further optimization studies.

Figure 3:
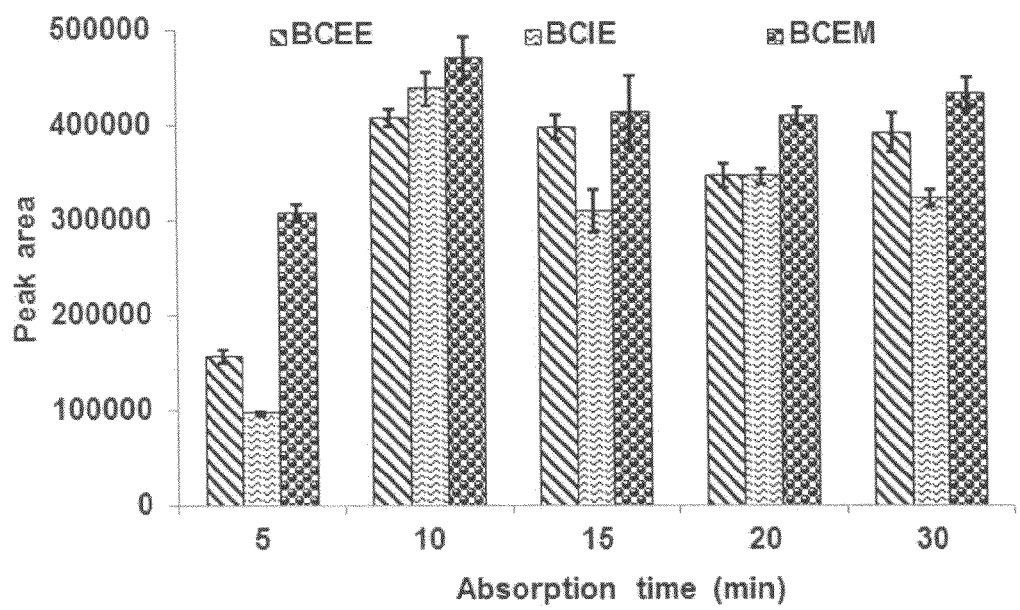
FIG. 3 is a graph of the effect of absorption time on a fully automated FA-SPME/GC-MS system.

The effect of the absorption time profile using CW/DVB fiber was examined in the range between 5 and 30 min. Peak areas are plotted against absorption time and shown in FIG. 3. FIG. 3 is a graph of the effect of absorption time on fully automated FA-SPME/GC-MS (extraction conditions; 100 mL of sample spiked with 100 ng $L^{-1}$ CEs, desorption time 3 min, sample flow rate of 50 mL $min^{-1}$ and sample pH 5.7). The equilibrium period was 10 min for all CEs; thus an absorption time of 10 min was selected for further optimization.

Figure 4:
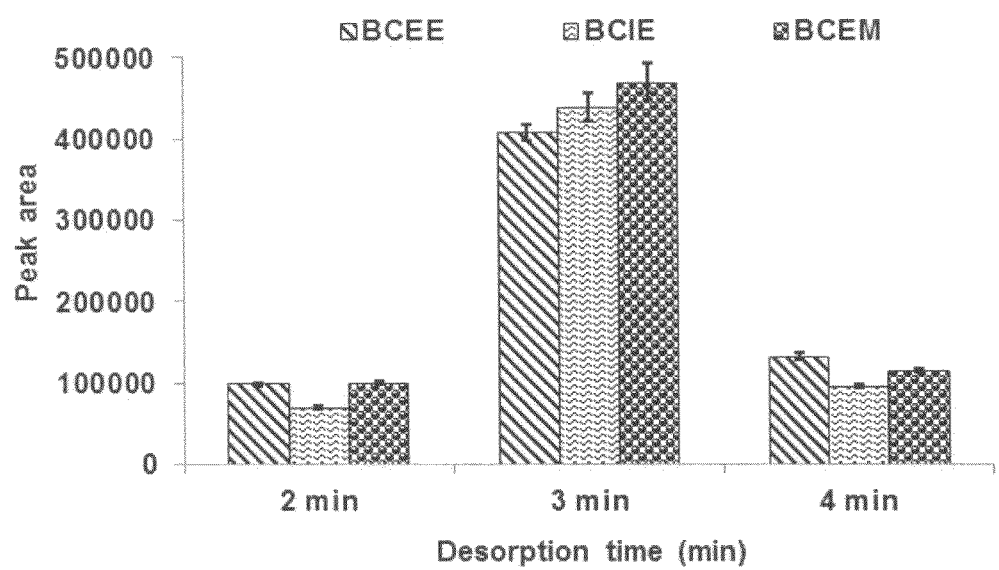
FIG. 4 is a graph of the effect of desorption time on a fully automated FA-SPME/GC-MS system.

In order to ensure complete desorption of analytes from the SPME fiber and avoid carryover, suitable desorption temperature and desorption time was measured. For this reason, desorption temperature of extracted analytes was carried out inside the GC injection port at temperatures 280° C. Also optimized by placing the fiber inside the GC injection port for a period of 3 to 5 min desorption time. FIG. 4 is a graph of the effect of desorption time on fully automated FA-SPME/GC-MS (extraction conditions; 100 mL of sample spiked with 100 μg $L^{-1}$ CEs, absorption time 10 min, sample flow rate 50 mL $min^{-1}$ and sample pH 5.7). FIG. 4 shows the best efficiency at 3 min desorption time. After analytes desorption, between the runs the SPME fibers were further cleaned at 280° C. for 3 min in CombiPAL SPME conditioning station. This was to ensure a complete fiber cleanup and avoid any sample carryover.

Figure 5:
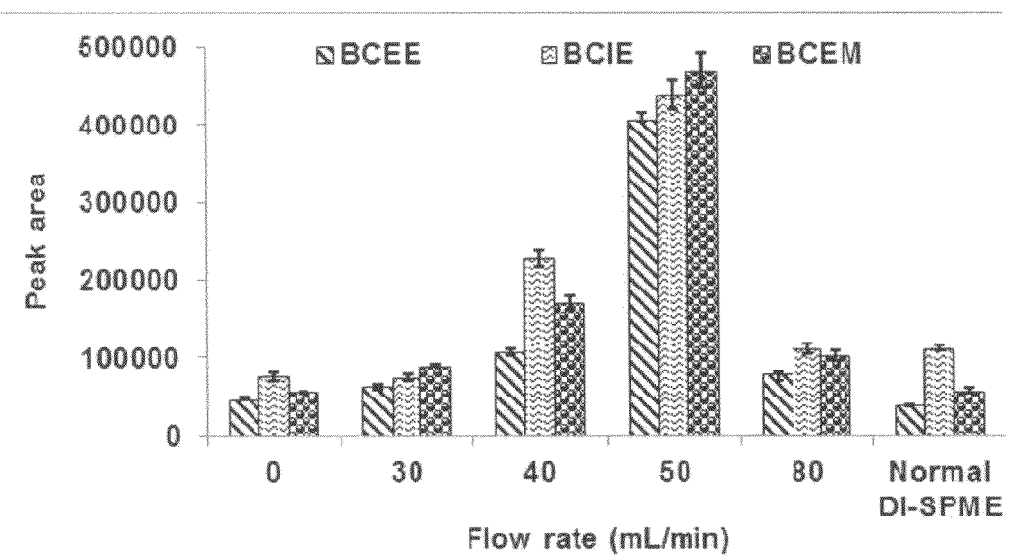
FIG. 5 is a graph of the influence of sample flow rate and conventional agitation on a fully automated FA-SPME/GC-MS system.

Precise peristaltic pump was employed to provide continuous full-automated FA-SPME technique. The aim was to investigate the effect of sample flow rate on the extraction efficiency of CEs. The flow rate of pump is an important parameter that permits continuous exposure of the SPME fiber to fresh aqueous sample. The flow rate of samples was examined in the range between 0 (static mode) and 80 mL $min^{-1}$. FIG. 5 is a graph of the influence of sample flow rate and conventional agitation on fully automated FA-SPME/GC-MS (extraction conditions for FA-SPME is as FIG. 4 with desorption time of 3 min. For conventional agitation-SPME, 20 mL sample was spiked with 100 μg $L^{-1}$ CEs, absorption time 10 min, desorption time 3 min, sample pH 5.7 and agitation speed of 250 rpm). FIG. 5 shows the extraction efficiency increased with increasing flow rate from 30 to 50 mL $min^{-1}$. A decrease in extraction efficiency at higher flow rates (>50 mL $min^{-1}$) was observed it is likely either the SPME fiber might has reached maximum extraction or high flow rates of sample causes loss of analytes from the SPME fiber resulting in back migration of the analytes and thus leading to lower pre concentration.

To compare the performance of FA-SPME, fully automated conventional SPME experiments were conducted using 20 mL regular autosample vial with sample agitation speed of 250 rpm for 10 min. Results clearly indicated that the use of flow instead of conventional agitation provided high sensitivity (FIG. 5). Thus FA-SPME is clearly advantageous for on-site applications, real sample can be directly analysed without sub sampling in a sample vials, the FA-SPME approach is more robust and user-friendly.

Figure 6:
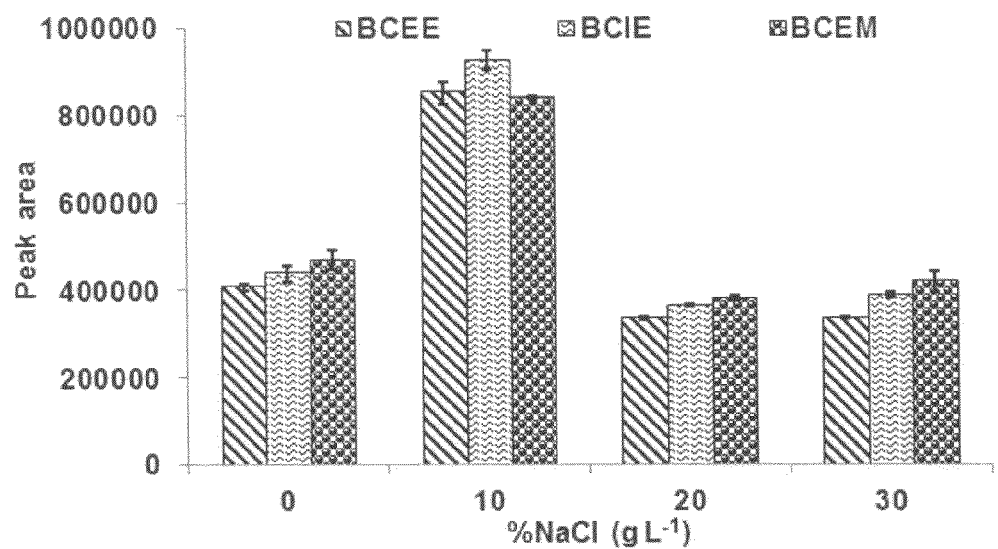
FIG. 6 is a graph of the effect of ionic strength on a fully automated FA-SPME/GC-MS system.

The effect of ionic strength on the extraction efficiency of full-automated FA-SPME was investigated by adding NaCl concentrations ranging from 0 (no salt addition) to 30% (w/v) as shown in FIG. 6. FIG. 6 is a graph of the effect of ionic strength on fully automated FA-SPME/GC-MS (extraction conditions; 100 mL of sample spiked with 100 μg $L^{-1}$ CEs, absorption time 10 min, desorption time 3 min, sample flow rate 50 mL $min^{-1}$ and sample pH 5.7). The highest extraction efficiency CEs was at 10% (w/v) concentration of NaCl. The extraction efficiency decreased for solution contain higher than 10% (w/v). The anomalous effect of NaCl on the extraction of CEs is probably due to two factors. The first is a salting-out effect, which decreases the solubility of the analytes, and thus increase the absorption. Secondly, salt dissolved in the solution may change the physical properties of the static aqueous layer on the fiber, and thereby reduce the rate of diffusion of the analyte through the static aqueous layer to the fiber. Therefore 10% (w/v) NaCl was added in the subsequent studies.

Figure 7:
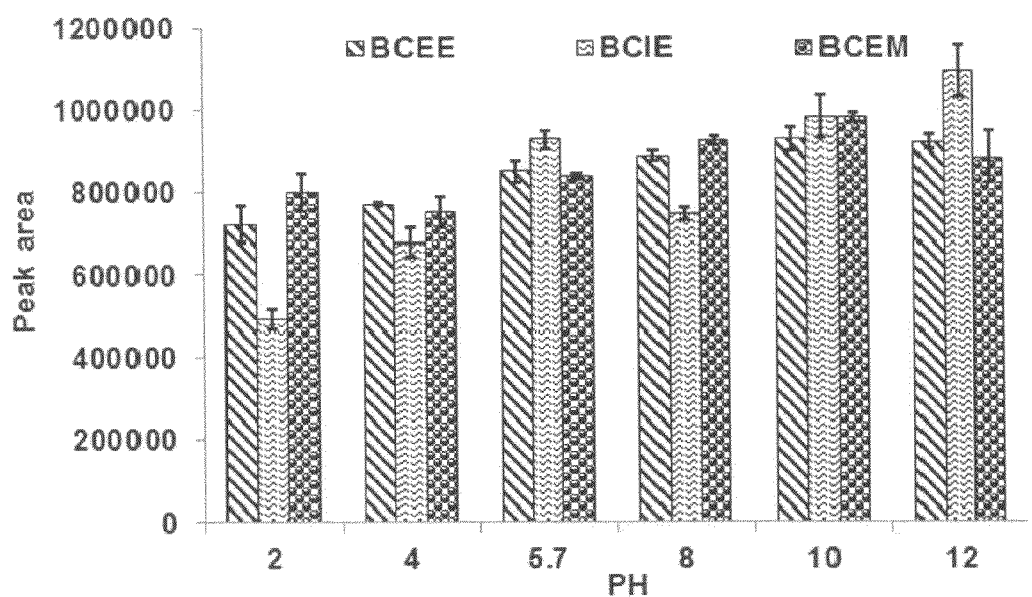
FIG. 7 is a graph of the effect of sample pH on a fully automated FA-SPME/GC-MS system.

To determine the effects of pH on the performance of FA-SPME, samples at different pH between 2 and 12 were investigated. The extraction performance was increases with increasing sample pH as shown in FIG. 7. FIG. 7 is a graph of the effect of sample pH on fully automated FA-SPME/GCMS (extraction conditions; 100 mL of sample spiked with 100 μg $L^{-1}$ CEs, absorption time 10 min, desorption time 3 min, sample flow rate 50 mL $min^{-1}$ and 10% of NaCl).

To evaluate the quantitative performance of the FA-SPME, the linear range, repeatability, and the limits of detection were investigated under the optimized conditions. The results are summarized in Table 2. Table 2 is presented below.

TABLE 2

Feature of the full-automated FA-SPME method. Linear range, coefficient of determination ($R^2$), linear equations, % RSD, LODs.

| Compound | Linearity range μg $L^{-1}$ | $R^2$ | Equation | RSDs, % (n = 3) | LODs μg $L^{-1}$ |
|---|---|---|---|---|---|
| BCEE | 0.5-100 | 0.996 | y = 0.0001x − 5.2102 | 6.2 | 0.041 |
| BCIPE | 0.5-100 | 0.980 | y = 0.0001x − 19.260 | 1.2 | 0.053 |
| BCEXM | 0.5-100 | 0.994 | y = 0.0001x − 4.3162 | 2.3 | 0.017 |

Excellent linearity was observed over the concentration range of 0.5-100 μg $L^{-1}$ with favorable coefficient of determination ($R^2$) ranging from 0.980 to 0.996. The repeatability study was carried out by extracting spiked water samples at a different concentration level of (0.5, 1, 5, 10, 20, 40, 70, 100 μg $L^{-1}$), and the average percentage relative standard deviations (% RSDs) were between 1.2 and 6.2% (n=3). The LODs, based on a (S/N ratio of 3, were ranged from 0.017 to 0.053 μg $L^{-1}$ were obtained. These results confirmed that the proposed method is suitable for trace level analysis of CEs in aqueous samples. A comparison of the main characteristics of the proposed method with previously reported works is summarized in Table 3). Table 3 is presented below.

TABLE 3

Comparison of the proposed method with other previously reported.

| Analytical technique | Sample | % Salt g L$^{-1}$ | Extraction time (min) | % RSDs | LODs µg L$^{-1}$ | % Recovery | Ref- |
|---|---|---|---|---|---|---|---|
| HF[b]-LPME/GC-FID | Water | 0 | 30 | 10.8-11.5 | 4.28-4.3 | 93-95 | Jing-Shan, et al. |
| HF-LPME/GC-ECD[c] | Water | 0 | 30 | 8.4-9.7 | 0.25-0.33 | 93-95 | Sahng-Da, et al. |
| SPME/GC-FID | Water | —[e] | 10 | 10 13 | 0.82-480 | —[e] | Sahng-Da, et al. |
| SPE/GC-FID[a] | Water | 0 | 80 | 0.9-6.5 | 0.001-0.003 | 73.4-80.9 | Wennrich, et al. |
| LPE/GC-FID | Water | 0 | 30 | 0.3-4.9 | 0.1-0.3 | 34.4-48.5 | Wennrich, et al. |
| SPME/GC-MS | Water | 0 | 10 | —[e] | 0.18-0.22 | —[e] | Wennrich, et al. |
| SPME/GC-FID | Water | 35 | 30 | 2-2.2 | 0.7-1.2 | —[e] | Wennrich, et al. |
| FA-SPME/GC-MS | water | 10 | 10 | 1.2-6.2 | 0.017-0.053 | 88.2-107.7 | Present |
| FA-SPME/GC-MS | Urine | 10 | 10 | 1.2-6.3 | 0.017-0.053 | 92.6-106.2 | Present |

The developed method showed promising results compared with previously reported microextraction methods. An important advantage of the present work over other microextraction techniques is a simple, solvent-free preconcentration system with high precision and low detection limits.

The applicability of the proposed FA-SPME technique for real water and urine sample matrices were evaluated. Dilution of the urine sample (1:1 ratio of dilution with ultrapure water) was carried out prior to the fully automated extraction. Concentrations of CEs in water and urine samples are shown in Table 4. Table 4 is presented below.

TABLE 4

The concentration of CEs in real samples that determined by proposed method.

| | Drinking water | | Tap water | | Human urine | |
|---|---|---|---|---|---|---|
| Cpds. | µg L$^{-1}$ | RSDs, % | µg L$^{-1}$ | RSDs, % | µg L$^{-1}$ | RSDs, % |
| BCEE | 5.5 | 0.54 | 3.1 | 0.35 | 30.8 | 4.6 |
| BCIE | 7.4 | 0.39 | 4.3 | 0.85 | 48.26 | 2.1 |
| BCEM | 6 | 0.12 | 7.6 | 0.83 | 11.5 | 3.88 |

To evaluate the matrix effects, one of the water and urine samples were spiked and recoveries were calculated based on standard addition method and shown in Table 5. Table 5 is presented below.

TABLE 5

Extraction recovery of CEs from water and human urine samples spiked by (5 and 20 µg L$^{-1}$) using full-automated flow system FA-SPME/GC-MS.

| | % Recovery ± RSDs, % | | | | | |
|---|---|---|---|---|---|---|
| | Drinking water | | Tap water | | Human urine | |
| Cpds. | 5 µg L$^{-1}$ | 20 µg L$^{-1}$ | 5 µg L$^{-1}$ | 20 µg L$^{-1}$ | 5 µg L$^{-1}$ | 20 µg L$^{-1}$ |
| BCEE | 98.4 ± 1.3 | 95.1 ± 4.1 | 101.6 ± 6.9 | 92.7 ± 6.2 | 105.7 ± 8.1 | 98.8 ± 5.7 |
| BCIE | 107.7 ± 3.6 | 91.6 ± 2.0 | 88.2 ± 4.2 | 94 ± 4.5 | 97.8 ± 1.0 | 92.6 ± 2.7 |
| BCEM | 104.9 ± 10 | 90.7 ± 3.0 | 93.4 ± 2.5 | 98.5 ± 5.7 | 95 ± 4.0 | 106.2 ± 7.6 |

The data clearly shows that high recovery, with % RSDs less than 10%. The excellent results demonstrated that the matrix effect had a negligible effect on FA-SPME. FIGS. 8A-8D are chromatograms of the total ion chromatograms of three CEs in real samples extracted by fully automated FA-SPME/GC-MS (A: drinking water spiked with 20 µg L$^{-1}$ of CEs, B: unspiked drinking water, C: unspiked urine, D: urine sample spiked with 20 µg L$^{-1}$ of CEs, peak identifications; 1: BCEE, 2; BCIE, 3: BCEM). FIGS. 8A-8D show the GC-MS chromatograms of extract from real water and urine samples and their respective spiked samples (at 5 and 20 µg L$^{-1}$). Direct extraction of urine sample could conceivably pose problems due to its complex sample matrix. The reason for dilution the urine samples in this work were increase the sample volume and to prevent the contamination of SPME fiber and increase the life of the fibers. Main objective of this work was on the fully automation of FA-SPME procedure and its applicability to large volume sample, this has clearly been demonstrated.

A novel fully automated flow assisted-SPME (FA-SPME) method was developed for the convenient analysis of chloroethers in large volume water and urine samples. With the use of a CTC CombiPal autosampler the fully automated SPME was enabled that allowed sample extraction, injection, and SPME fiber conditioning to be carried out completely automatically. This method provides satisfactory analyte enrichment, sensitivity, and reproducibility and suitable for real water and urine samples and offers the potential of implementing a fully automatic onsite sample preparation GC-MS platform. Moreover, the use of FA-SPME instead of conventional agitation-SPME provided high sensitivity for the determination of CEs in large volume real samples. This automated flow assisted-SPME approach demonstrated the feasibility of a complete analytical system comprising sample preparation and GC-MS that might be operated onsite, fully automatically without human intervention.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A flow assisted-solid phase microextraction/gas chromatography-mass spectrometry (FA-SPME/GC-MS) system, comprising:
    a sample container comprising a sample solution comprising an aqueous solution and analytes;
    a first tube that connects the sample container and a pump and transports the sample solution to the pump;
    a second tube that transports sample solution to an extraction vial;
    an autosampler that uses the extraction vial to extract an aliquotted sample through an automated SPME method to determine the chloroether content in the aliquotted sample;
    a gas-chromatograph that desorbs the SPME fiber and determines the content of one or more chloroethers in the aliquotted sample; and
    a third tube that circulates the aliquotted sample from the extraction vial to the sample container.

2. The system of claim 1, wherein the system is fully-automated and no manual operation is required during the extraction process.

3. A method for determination of chloroethers in a sample, comprising:
    directly contacting an SPME fiber with an aqueous sample to form an enriched SPME sample,
        wherein the aqueous sample comprises one or more chloroethers and the contacting is carried out with a single pass of a flowing stream of the aqueous sample; and
    desorbing the chloroethers from the enriched SPME sample and determining the content of the chloroethers in the sample with the flow assisted-solid phase microextraction/gas chromatography-mass spectrometry (FA-SPME/GC-MS) system according to claim 1.

4. The method of claim 3, wherein:
the desorbing is carried out inside a sample port of the gas chromatograph to obtain a desorbed analyte composition; and
the desorbed analyte composition is chromatographed in the gas chromatograph.

5. The method of claim 3, wherein:
during the contacting the aqueous sample is not recirculated over the SPME fiber.

6. The method of claim 3, wherein:
the contacting, desorbing and determining are carried out consecutively.

7. The method of claim 3, wherein the contacting, desorbing, and determining are fully automated and no manual operation is required.

8. The method of claim 3, wherein at least 100 mL of the aqueous sample is contacted with SPME fibers.

9. The method of claim 2, wherein:
the SPME fiber is a polyethylene glycol/divinylbenzene fiber;
the desorbing of the analyte composition from the enriched SPME sample occurs over a time period between 2-4 minutes; and
the analytes are extracted by the SPME fiber in direct immersion mode for 8-11 minutes.

* * * * *